United States Patent [19]

Edgar et al.

[11] Patent Number: 4,772,747
[45] Date of Patent: Sep. 20, 1988

[54] PREPARATION OF 2,4,6-TRICHLOROPHENYLHYDRAZINE

[75] Inventors: Kevin J. Edgar; John A. Hyatt, both of Kingsport, Tenn.

[73] Assignee: Eastman Kodak Company, Rochester, N.Y.

[21] Appl. No.: 546,707

[22] Filed: Oct. 28, 1983

[51] Int. Cl.$^4$ ............................................. C07C 109/04
[52] U.S. Cl. .................................. 564/314; 544/237; 548/475; 564/310
[58] Field of Search ....................... 564/310, 314, 412; 548/475; 544/237

[56] References Cited

U.S. PATENT DOCUMENTS

| | | | |
|---|---|---|---|
| 2,495,000 | 1/1950 | Hanford | 548/475 X |
| 2,675,409 | 4/1954 | Orloff et al. | 564/412 |
| 2,973,386 | 2/1961 | Weldon | 564/412 X |
| 2,995,567 | 8/1961 | Sarett et al. | 564/314 X |
| 3,375,273 | 3/1968 | Drain et al. | 548/475 X |
| 3,734,925 | 5/1973 | Minieri | 548/475 |
| 3,962,336 | 6/1976 | Lademann et al. | 564/412 |
| 4,447,647 | 5/1984 | Werner et al. | 564/412 |

OTHER PUBLICATIONS

Borisavljevic et al., "Chemical Abstracts", vol. 60, pp. 5390–5391 (1964).
Manfred et al., "Chemical Abstracts", vol. 79, p. 376, Section No. 137069e (1973).

Primary Examiner—Robert V. Hines
Attorney, Agent, or Firm—J. Frederick Thomsen; Daniel B. Reece, III

[57] ABSTRACT

Disclosed is a process for the preparation of 2,4,6-trichlorophenylhydrazine by chlorinating the reaction product of phenylhydrazine and a dicarboxylic anhydride to obtain an N-(2,4,6-trichloroanilino)dicarboximide which is reacted with a base capable of liberating 2,4,6-trichlorophenylhydrazine therefrom.

5 Claims, No Drawings

PREPARATION OF 2,4,6-TRICHLOROPHENYLHYDRAZINE

DESCRIPTION

This invention concerns a novel process for the preparation of 2,4,6-trichlorophenylhydrazine.

A conventional means for the synthesis of 2,4,6-trichlorophenylhydrazine comprises the steps of (1) chlorinating aniline to obtain 2,4,6-trichloroaniline, (2) diazotizing the 2,4,6-trichloroaniline to obtain the diazonium salt thereof, (3) reducing the diazonium salt by treating it with an alkali sulfite to obtain a 2,4,6-trichlorophenylhydrazinesulfamic acid salt, (4) decomposing the sulfamic acid salt to a hydrazinium salt such as a chloride or sulfate by treating the former with an acid, and (5) converting the hydrazinium salt to 2,4,6-trichlorophenylhydrazine. This burdensome procedure generates a considerable amount of by-products such as inorganic salts, sulfur dioxide, and polychlorinated biphenyls which not only must be disposed of, some by special means, but also require unusual precautions to avoid exposure to workers.

The process of our invention provides a simpler, and thus more economical, means for the preparation of 2,4,6-trichlorophenylhydrazine. In its broader aspects our novel process comprises the steps of (1) reacting phenylhydrazine with a dicarboxylic anhydride to obtain a reaction product comprising an N-anilino dicarboximide having the structure

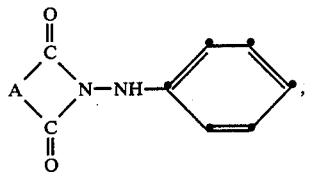

an N-phenylazinedione having the structure

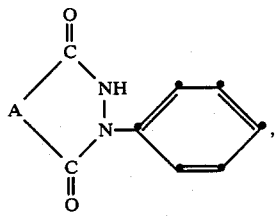

or a mixture thereof;

(2) chlorinating the reaction product to obtain an N-(2,4,6-trichloroanilino)dicarboximide; and (3) reacting the N-(2,4,6-trichloroanilino)dicarboximide with a base capable of liberating 2,4,6-trichlorophenylhydrazine from the N-(2,4,6-trichloroanilino)-dicarboximide; wherein A is the residue of a dicarboxylic acid.

Even though the cost of the phenylhydrazine starting material is significantly greater than aniline, our novel process offers economic advantages due to its relative simplicity. Additionally, the use of our process permits by-product formation to be reduced substantially.

Although the overall process includes the initial step of reacting phenylhydrazine with a dicarboxylic anhydride, the intermediates obtained therefrom are, in general, known compounds. Thus, the process of our invention is particularly concerned with the second and third steps described above.

The first step of the process is carried out by reacting phenylhydrazine with a dicarboxylic anhydride at elevated temperature in the presence of an inert organic diluent or solvent under essentially anhydrous conditions. Examples of dicarboxylic anhydrides that may be used include phthalic, tetrahydrophthalic, hexahydrophthalic, succinic, glutaric, and maleic anhydrides and alkyl derivatives thereof. Normally the most economical anhydrides such as tetrahydrophthalic and, especially, phthalic anhydrides are used. However, when it is desired to produce, as described hereinafter, a coproduct dicarboximide containing a particular dicarboxylic acid residue, it may be advantageous to use a more costly anhydride in the first step of our process. Carboxylic acids such as acetic and propionic acid, hydrocarbons such as hexane, heptane, benzene, toluene and xylene, chlorinated hydrocarbons such as dichloromethane, 1,2-dichloroethane, 1,2-dichloropropane, 1,1,1-trichloroethane, tetrachloroethylene, chlorobenzene and o-dichlorobenzene, and alkanols such as ethanol, propanol and the butanols are examples of organic diluents that may be used in the reaction of phenyl hydrazine with a dicarboxylic anhydride.

The resulting reaction solution containing the N-anilinodicarboximide, the N-phenylazinedione, or a mixture thereof may be used directly in the chlorination step. However, when biphenyl is present as an impurity in the phenylhydrazine, it is normally preferred to separate those intermediates from the initial reaction mixture, for example, by cooling to precipitate the intermediates and filtering. The biphenyl remains in solution and is removed from the process thereby minimizing the formation of chlorinated biphenyls.

The chlorination step is carried out by treating the N-anilinodicarboximide and/or N-phenylazinedione with a chlorinating agent such as sulfuryl chloride or, preferably, chlorine in the presence of an inert solvent, e.g. one of those described hereinabove for the phenylhydrazine-dicarboxylic anhydride reaction. If desired, a portion, e.g. up to about 10 weight percent, of the water-miscible organic solvents or diluents can consist of water. Because of its cost and effectiveness, acetic acid is the preferred solvent.

The chlorination may be conducted at a temperature of about 0° to 100° C. although temperatures of about 15° to 50° C. normally will be used. It is apparent that the amount of chlorinating agent used will be at least three moles per mole of N-anilinocarboximide and/or N-phenylazinedione. While it is preferred to employ only a slight excess, e.g. up to about 10 mole percent, of chlorinating agent, the use of significantly larger amounts does not adversely affect production of the desired N-(2,4,6-trianilino)dicarboximide.

The N-(2,4,6-trichloroanilino)dicarboximide obtained from the chlorination step normally is isolated from the chlorination reaction mixture by precipitation and liquid-solid separation, e.g. filtration or centrifugation. The 2,4,6-trichlorophenylhydrazine then is obtained by reacting, in the presence of one or more inert, organic solvents, the N-(2,4,6-trichloroanilino)dicarboximide with a base that is capable of liberating or releasing the former from the latter. Typical basic compounds that may be used include alkali metal hydroxides, bicarbonates and carbonates and nitrogen-containing compounds such as ammonia, primary amines and diamines, particularly aliphatic amines and diamines, hydrazine and substituted hydrazines such as phenylhydrazine. Preferred nitrogen-containing bases have the formulas $H_2N-R^1$, $H_2NNH-R^2$ and $H_2N-R^3-NH_2$ wherein $R^1$ is hydrogen; alkyl of up to about 20 carbon atoms which may be substituted with nonreactive substituents such as hydroxy, alkoxy, and the like; or cycloalkyl such as cyclohexyl; $R^2$ may be the same as $R^1$ or aryl such as phenyl, alkylphenyl and alkoxyphenyl; and $R^3$ is alkylene of up to about eight carbon atoms such as ethylene and hexamethylene. When the base is a nitrogen-containing compound, the reaction normally is carried out under essentially anhydrous conditions. The most preferred bases, especially when N-(2,4,6-trichlorophenyl)hydrazine is the sole product recovered, are the aliphatic amines, particularly butylamine and 2-aminoethanol since they are relatively inexpensive, normally-liquid compounds.

When an alkali metal base is used, the reactant(s) is saponified to give 2,4,6-trichlorophenylhydrazine and a dicarboxylic acid salt. When ammonia or a primary amine is used, a transimidation reaction occurs wherein the N-(2,4,6-trichloroanilino)dicarboximide is converted through an amide or hydrazide to 2,4,6-trichlorophenylhydrazine and a dicarboximide or an N-substituted dicarboximide which, depending on the particular dicarboxylic acid and amine residues present, may themselves be useful compounds. For example, N-(2-hydroxyethyl)phthalimide can be used as an intermediate in the azo dyes disclosed in U.S. Pat. No. 3,525,733. The use of hydrazine or a substituted hydrazine results in the liberation of 2,4,6-trichlorophenylhydrazine through a similar reaction with the coproduction of an N-aminodicarboximide and/or an azinedione or an N-substituted-aminodicarboximide and/or an N-substituted-azinedione. Utilization of phenylhydrazine as the base not only gives 2,4,6-trichlorophenylhydrazine but regenerates the N-anilinodicarboximide and/or N-phenylazinedione used in the chlorination step. The overall reactions involved in this step of our process in which 2,4,6-trichlorophenylhydrazine is formed when using a nitrogen-containing base are

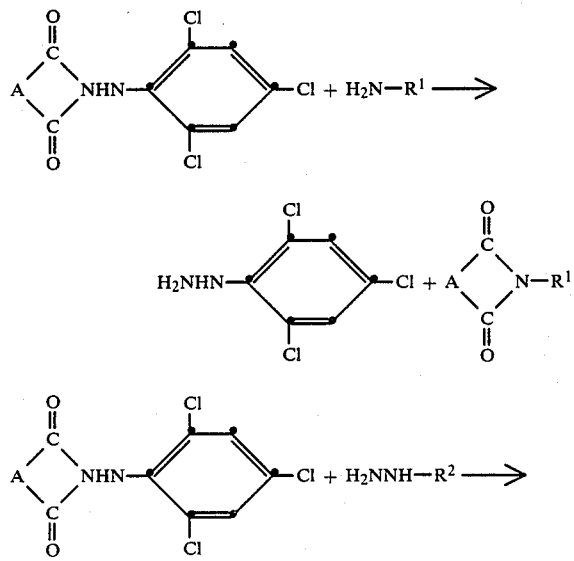

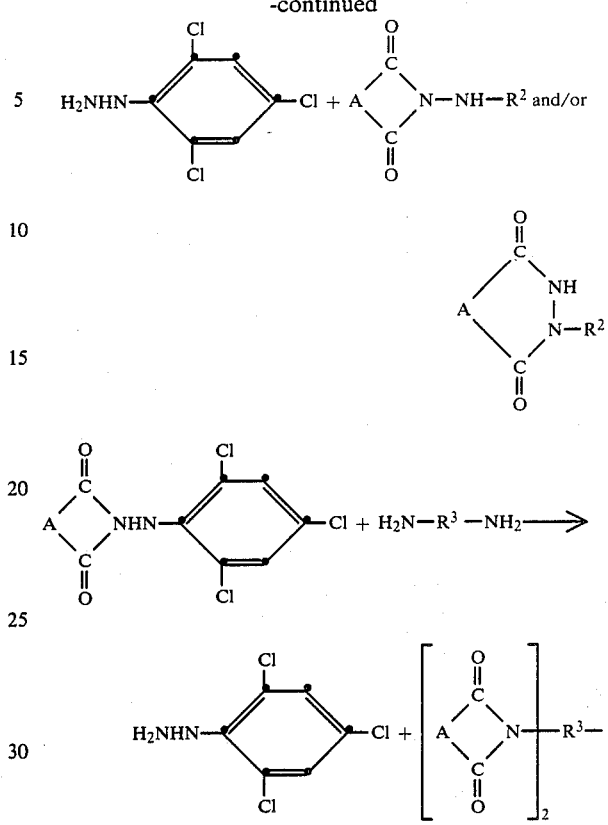

wherein A, $R^1$, $R^2$ and $R^3$ are as defined above.

Usually at least one equivalent of base, e.g. one mole of primary amine or hydrazine and 0.5 mole of diamine, is used per mole of N-(2,4,6-trichloroanilino)dicarboximide with an excess of up to about 20 mole percent normally being used to maximize conversion of the N-(2,4,6-trichloroanilino)dicarboximide. The temperature at which the reaction of the base and N-(2,4,6-trichloroanilino)dicarboximide may be carried out will vary considerably depending on the particular base employed. Generally, temperatures within the range of about 20° to 150° C., using an appropriate solvent, will produce satisfactory results. When a nitrogen-containing base is used, the initial reaction in which an amide/hydrazide is formed should be carried out at a temperature which is sufficiently high to effect reaction of the base with the N-(2,4,6-trichloroanilino)dicarboximide but at which loss of the base through vaporization is minimized. This initial temperature usually will be within the range of about 25° to 75° C. To complete the reaction whereby a dicarboximide or azinedione is formed and the release of 2,4,6-trichlorophenylhydrazine is completed, the reaction mixture should be heated to a temperature of at least 50° C., preferably in the range of about 80° to 100° C.

The reaction of the N-(2,4,6-trichloroanilino)dicarboximide and base may be carried out in the aqueous phase when using an alkali metal compound or in an inert, organic solvent when employing a nitrogen-containing compound. Hydrocarbons and chlorinated hydrocarbons such as those mentioned above and, to a lesser extent, alkanols are typical of such organic solvents. As is illustrated below a combination of solvents can be used to recover the 2,4,6-trichlorophenylhydrazine as an essentially pure solid, i.e. essentially free of dicarboximide and/or azinedione.

The process of our invention is further illustrated by the following examples.

EXAMPLE 1

To a stirred slurry of phthalic anhydride (37.7 g) in acetic acid (175 mL) in a 500-mL, three-necked flask was added, dropwise, phenylhydrazine (25.0 g) with the exotherm raising the temperature from 20° C. to 38° C. The resulting yellow solution was heated to 95°–100° C., held at that temperature for three hours, and then cooled to 20° C. After the rapid, dropwise addition of water (15 mL) chlorine was added through a straight, glass tube over a period of two hours while maintaining the temperature at 20°–25° C. by means of an ice-water bath. The product began to precipitate early in the chlorination and by the time 50–65% of the chlorine had been added, the reaction mixture was a heavy yellow slurry. After the required amount (about 54.1 g) of chlorine was added, thin layer chromatography showed the reaction to be essentially complete. The reaction mixture then was degassed by sparging with nitrogen for one hour, cooled and the product was collected by filtration. The product was washed with methanol and vacuum dried at 40° C. to give 65.0 g of pale yellow crystals which consisted of 95.0% N-(2,4,6-trichloroanilino)phthalimide, 4.1% N-(2,4-dichloroanilino)phthalimide and 0.3% N-(2,6-dichloroanilino)phthalimide according to gas chromatography analysis.

Normally, the product will be held methanol-wet for conversion to 2,4,6-trichlorophenylhydrazine.

EXAMPLE 2

Phthalic anhydride (50.0 g) was reacted with phenylhydrazine (33.2 g) in acetic acid (100 mL) according to the procedure described in Example 1 but using a reaction time of one hour at 95°–100° C. The reaction mixture was allowed to cool to 30° C., then cooled to 15° C. and the product was isolated by filtration. A sample of the wet filter cake was dried to determine the percent solids and for analysis. The yield of product, consisting of 70.9% N-anilinophthalimide [2-(phenylamino)-1H-isoindole-1,3(2H)-dione] and 27.6% 2-phenyl-1,4-phthalazinedione, was 80–85%. By using the filtrate in subsequent batches, the yield can be increased to 90–96%.

The product (40.0 g dry material, acetic acid wet) in a mixture of acetic acid (100 mL) and water (10 mL) was treated with chlorine (~40 g), the reaction mixture was degassed and cooled, and the product was isolated by filtration, washed and dried according to the procedure described in Example 1. Gas chromatography analysis established that the product (45.5 g, pale yellow crystals) consisted of 96% N-(2,4,6-trichloroanilino)phthalimide.

EXAMPLE 3

A mixture of toluene (60 mL), methanol (15 mL), and N-(2,4,6-trichloroanilino)phthalimide (15.0 g) in a 500-mL, three-necked flask was heated to 65°–70° C. and butylamine (3.5 g) was added dropwise over 15 minutes at 65°–70° C. The mixture was agitated at 65°–70° C. for 30 minutes and then was heated to distill off methanol-toluene azeotrope (20 mL collected) to a pot temperature of 90° C. The solution was held at 90° C. for two hours, then was cooled over one hour to 20° C. and then quickly to 0°–5° C. The slurry was filtered and the product was washed with heptane and vacuum-dried at 40° C. to give 9.5 g of tan needles which consisted of 97.2% 2,4,6-trichlorophenylhydrazine.

EXAMPLE 4

Using the procedure described in Example 3 phenylhydrazine (4.7 g) was added dropwise over a 30 minute period to a mixture of toluene (100 mL) and N-(2,4,6-trichloroanilino)phthalimide. After heating the reaction mixture at reflux thin layer chromatography established the presence of 2,4,6-trichlorophenylhydrazine in the mixture.

EXAMPLE 5

To a 500-mL, stainless steel autoclave were charged 200 mL isopropanol, 40.0 g N-(2,4,6-trichloroanilino)phthalimide and about 10.0 g ammonia gas. The mixture was heated to 100° C., held at 100° C. for 8.7 hours and then cooled to 20° C. Thin layer chromatography showed a large spot corresponding to 2,4,6-trichlorophenylhydrazine and no starting material. The reaction mixture was transferred to a 500-mL, three-necked flask and 240 mL distillate was removed at 20°–110° C. pot temperature with 100 mL portions of toluene being added after ⅓ and ⅔ of the distillate had been removed. Then 100 mL water and 10 mL 50% aqueous sodium hydroxide were added and the resulting mixture was heated to 80° C. to effect separation of the layers. Water (100 mL) was added to the upper layer, the layers were heated to 80° C., and the mixture was filtered at 80° C. The layers were separated and the organic phase was charged to another 500-mL, three-necked flask equipped with a thermometer, mechanical stirrer, Dean-Stark trap and condenser. After stripping off 80 mL toluene/water azeotrope, the residue was cooled to 0° C. and filtered. The crude product obtained was washed with 20° C. heptane and then vacuum dried at 40° C. to give 7.0 g of pale yellow crystals which assayed 94.1% 2,4,6-trichlorophenylhydrazine.

EXAMPLE 6

A mixture of 15 mL methanol, 15 mL water, 15.0 g N-(2,4,6-trichloroanilino)phthalimide and 4.1 g 40% aqueous methylamine was heated at 35–40° C. for three hours and then at reflux for seven hours under a positive nitrogen pressure. The reaction mixture was cooled to 20° C., 150 mL water was added dropwise and the resulting slurry was cooled to 0° C. The solids were filtered off, washed with water and vacuum dried at 40° C. to give 9.0 g of pale yellow crystalline product which assayed 70.3% 2,4,6-trichlorophenylhydrazine.

EXAMPLE 7

A mixture of 33.0 g succinic anhydride, 36 g phenylhydrazine and 100 mL acetic acid was heated at reflux for 16 hours. Thin layer chromatography showed no starting material and formation of two products in a ratio of about 3:1. The reaction mixture was stripped of solvent in vacuo and the crude product was recrystallized from ethanol to give 35.0 g (56%) of the major product, N-anilinosuccinimide, as white needles, mp 155°–7° C. A mixture of 19.0 g of this product and 75 mL acetic acid was treated with chlorine until uptake ceased. The reaction mixture was stripped of solvent and the residue was recrystallized from ethanol to give 24.3 g (83%) of N-(2,4,6-trichloroanilino)succinimide, mp 114°–5° C. A mixture of 5.0 g of the trichloro intermediate, 1.25 g 2-aminoethanol, 25 mL toluene and 5 mL methanol was heated at reflux for 72 hours. The mixture was diluted with ethyl acetate, extracted with 10% hydrochloric acid and the aqueous phase was separated and neutralized with 10% aqueous sodium hydroxide. The precipitated product was filtered off, washed with water and air dried to give 2.41 g (67%) 2,4,6-trichlorophenylhydrazine, mp 140°–2° C.

This invention has been described in detail with particular reference to preferred embodiments thereof, but it will be understood that variations and modifications can be effected within the spirit and scope of the invention.

I claim:

1. Process for the preparation of 2,4,6-trichlorophenyl hydrazine which comprises the steps of
   (1) reacting phenylhydrazine with a dicarboxylic anhydride to obtain a reaction product comprising an N-anilinodicarboximide having the structure

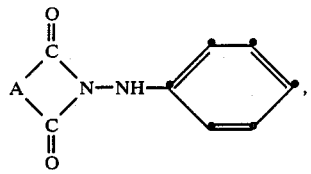

an N-phenylazinedione having the structure

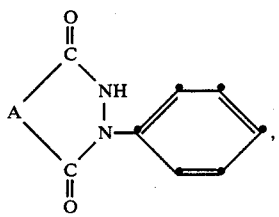

or a mixture thereof;
   (2) chlorinating the reaction product to obtain an N-(2,4,6-trichloroanilino)dicarboximide; and
   (3) reacting the N-(2,4,6-trichloroanilino)dicarboximide with a base capable of liberating 2,4,6-trichlorophenylhydrazine from the N-(2,4,6-trichloroanilino)dicarboximide; wherein A is the residue of a dicarboxylic acid.

2. Process according to claim 1 wherein the dicarboxylic anhydride is phthalic anhydride and the base is a nitrogen-containing compound having the formula $H_2N-R^1$, $H_2NNH-R^2$ or $H_2N-R^3-NH_2$ wherein $R^1$ is hydrogen, alkyl or cycloalkyl; $R^2$ is $R^1$ or aryl; and $R^3$ is alkylene.

3. Process for the preparation of 2,4,6-trichlorophenylhydrazine which comprises the steps of
   (1) chlorinating an N-anilinodicarboximide having the structure

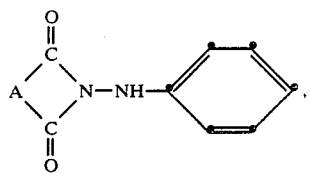

an N-phenylazinedione having the structure

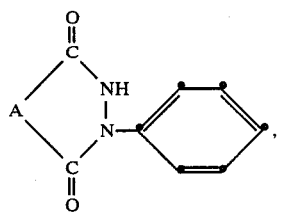

or a mixture to obtain an N-(2,4,6-trichloroanilino)dicarboximide; and
   (2) reacting the N-(2,4,6-trichloroanilino)dicarboximide with a base capable of liberating 2,4,6-trichlorophenylhydrazine from the N-(2,4,6-trichloroanilino)dicarboximide; wherein A is the residue of a dicarboxylic acid.

4. Process according to claim 3 wherein the dicarboxylic anhydride is phthalic anhydride and the base is a nitrogen-containing compound having the formula $H_2N-R^1$, $H_2NNH-R^2$ or $H_2N-R^3-NH_2$ wherein $R^1$ is hydrogen, alkyl or cycloalkyl; $R^2$ is $R^1$ or aryl; and $R^3$ is alkylene.

5. Process for the preparation of 2,4,6-trichlorophenylhydrazine which comprises the steps of
   (1) treating an N-anilinodicarboximide having the structure

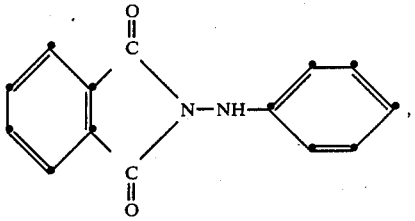

an N-phenylazinedione having the structure

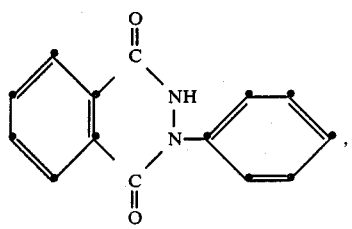

or a mixture thereof with chlorine at a temperature of about 15° to about 50° C. in the presence of acetic acid to obtain N-(2,4,6-trichloroanilino)phthalimide; and
   (2) reacting the N-(2,4,6-trichloroanilino)phthalimide with a nitrogen-containing compound having the formula $H_2N-R$ wherein R is an alkyl group having about 4 to about 20 carbon atoms.

* * * * *